(12) United States Patent
Shchervinsky et al.

(10) Patent No.: US 6,217,369 B1
(45) Date of Patent: Apr. 17, 2001

(54) ELECTRICAL CONNECTOR FOR CARDIAC DEVICES

(75) Inventors: Semyon Shchervinsky, Whitehouse Station; Claude O. Clerc; Alex Ilori, both of Flemington, all of NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/451,590

(22) Filed: Nov. 30, 1999

(51) Int. Cl.[7] .................................................. H01R 13/58
(52) U.S. Cl. ........................... 439/456; 439/909; 607/122
(58) Field of Search .................... 439/502, 456, 439/909, 834, 839, 745, 417, 743; 607/122, 128, 129, 132

(56) References Cited

U.S. PATENT DOCUMENTS

| | | | |
|---|---|---|---|
| 4,010,756 | 3/1977 | DuMont et al. | 607/132 |
| 4,341,226 | 7/1982 | Peters | 607/132 |
| 4,442,840 | 4/1984 | Wojciechowciz, Jr. | 607/132 |
| 4,541,440 | 9/1985 | Parsonnet | 607/132 |
| 4,633,880 | 1/1987 | Osypka et al. | 600/374 |
| 4,693,258 | 9/1987 | Osypka et al. | 607/116 |
| 5,217,027 | 6/1993 | Hermens | 607/126 |
| 5,241,951 | 9/1993 | Mason et al. | 607/104 |
| 5,241,957 | 9/1993 | Camps et al. | 607/119 |
| 5,314,463 | 5/1994 | Camps et al. | 607/129 |
| 5,366,496 | 11/1994 | Dahl et al. | 607/132 |
| 5,547,399 | 8/1996 | Naghi et al. | 439/623 |
| 5,632,770 | 5/1997 | Schaldach | 607/122 |
| 5,702,270 | * 12/1997 | Casica et al. | 439/909 |
| 5,792,217 | 8/1998 | Camps et al. | 607/119 |
| 5,795,178 | 8/1998 | Schilder et al. | 439/417 |

* cited by examiner

Primary Examiner—Tulsidas Patel

(57) ABSTRACT

A temporary cardiac pacing wire, or a similar device, includes an electrically conductive lead which is folded over on itself so as to be adapted for connection to a pacing or monitoring apparatus. In the case of a bipolar temporary cardiac pacing wire, flexible wires are employed having two elongated conductive sections at a proximal end. The conductive sections are suitable for connecting to a power source adapted to generate electrical signals for stimulating, pacing, sensing, monitoring or defibrillating the heart of a patient. One conductive section results from the distal end of a Keith-type needle that breaks away from the rest of the needle. This section is suitable for directly connecting to the power source. The other conductive section is suitable for connecting to the power source when folded over on itself.

22 Claims, 7 Drawing Sheets

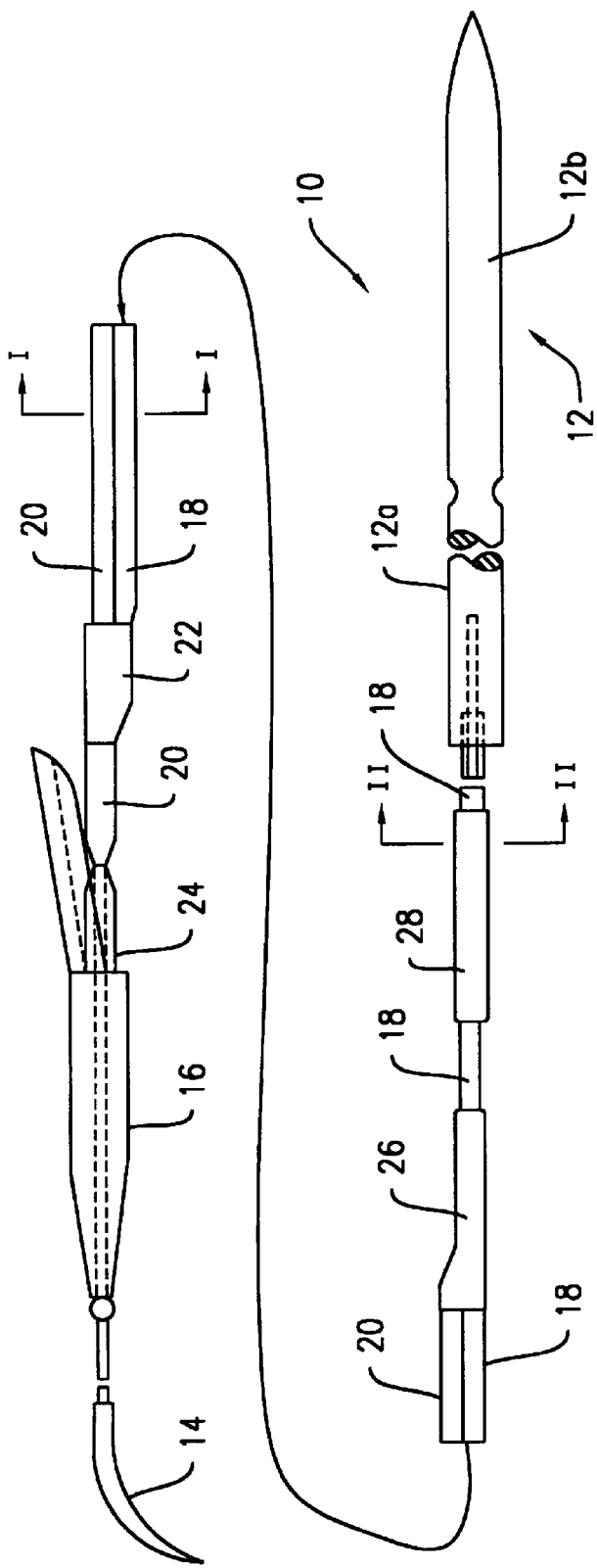
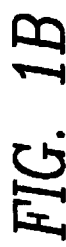

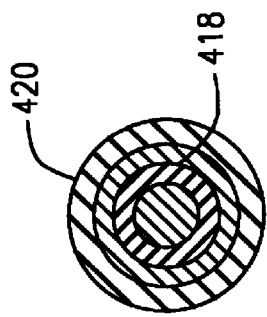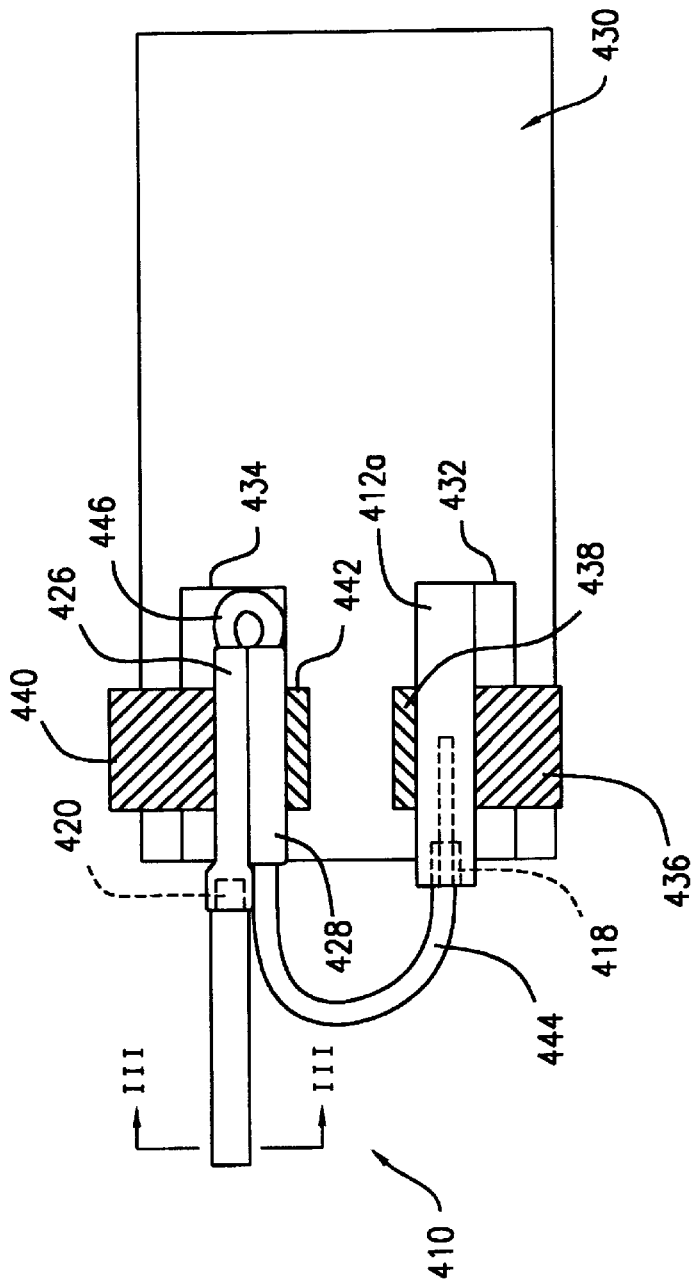

ELECTRICAL CONNECTOR FOR CARDIAC DEVICES

FIELD OF THE INVENTION

The present invention relates to electrical connectors for cardiac devices and, more particularly, to temporary cardiac pacing wires that are adapted for use with apparatus that generate electrical signals suitable for stimulating, pacing, sensing, monitoring or defibrillating the heart.

BACKGROUND OF THE INVENTION

Devices to stimulate or regulate cardiac function have been known and used for decades. They involve a power source (pacemaker) and one or more surgical electrodes to attach the source to the heart. They are generally of two types.

Implantable pacers are intended for long-term use and, as the name suggests, are entirely implanted in the body. The other type is intended for temporary use. The temporary pacemaker is located outside the body and is connected to the heart by a surgical electrode called a "temporary pacing wire." Although surgical electrodes are used for preparing electrocardiograms and other applications, for the sake of brevity, the description that follows is focused on temporary pacing wires.

In general, such wires are constructed of a number of fine, stainless steel wires braided or twisted together to form a single, flexible, multi-strand electrode wire. The major portion of the wire is electrically insulated with a polyethylene, polytetrafluoroethylene, silicon, nylon, or another non-conducting coating, with a short length of wire at either end left uninsulated. To the distal uninsulated end of the electrode wire there is attached, by swaging or other means, a fine curved needle for piercing the 5 heart tissue to place the uninsulated end of the electrode in the myocardium. At the proximal end of the electrode wire, a straight (e.g., Keith-type) cutting needle is attached for piercing the thoracic wall to lead the electrode to an outer point for connection with the pacemaker. Once that has been accomplished, the needle, or its sharp-pointed end, is clipped or broken off and the proximal end of the electrode is readied for attachment to the pacemaker as required to stimulate or regulate the beating of the heart. A single setup involves two electrodes, i.e., two temporary pacing wires. During the time that the temporary pacing wire is performing its function, the uninsulated end of the electrode must remain anchored in the myocardium. The anchorage must be secure, lest the continually beating heart cause the wire to be expelled from the myocardium. When the need for the pacing wire has passed, it is necessary to remove from the body the wire that runs from the external pacemaker to the myocardium.

The process of preparing the proximal ends of the pacing wires (electrodes) to the pacemaker requires numerous steps and is time consuming. Not only do the proximal ends of the pacing wires require removal from the Keith-like needles, but separate steps are required to make them suitably adapted for attachment to electrodes (terminals) within the pacemaker.

DESCRIPTION OF THE RELATED ART

U.S. Pat. No. 4,693,258, issued on Sep. 15, 1987 to Osypka et al., discloses an electrode connector assembly that can be used to electrically connect the proximal end of a pacing wire (with insulation removed) to the socket of a pacing or monitoring instrument. This approach is useful but requires many small parts to be assembled. This may prove to be difficult and time consuming to work with in the operating room environment. Also, multistrand wires have a tendency to fray which adds to difficulties. Additionally, small parts are prone to be easily lost.

U.S. Pat. No. 4,633,880, issued on Jan. 6, 1987 to Osypka et al., discloses an implantable bipolar electrode assembly where the two distal ends of the wire are received in an electrically conductive sleeve (pole). One wire is in electrical contact with the sleeve and the second wire passes through the sleeve. The distal end of the second wire is stripped of insulation to provide electrical contact with heart tissue. The stripped section is configured to introduce mechanical resistance to its removal from heart tissue. Although this electrode assembly is effective in delivering a bipolar signal to the heart, it is not intended for use as a direct electrical connection with a pacemaker.

U.S. Pat. No. 5,792,217, issued on Aug. 11, 1998 to Camps et al., discloses an arrangement in which the proximal ends of two pacing wires can be simultaneously broken away from a Keith-type needle. Affixed to the proximal end of each wire is an electrical connector that is suitably dimensioned to connect to a pacing or monitoring instrument. This arrangement requires complex manufacturing processes to fabricate. Because the Keith-type needle accommodates two electrical connectors in a side-by-side fashion, the needle is approximately twice as large as those typically used. The larger needle can cause undesirable tissue trauma.

In view of the foregoing, there is a need for a simple, efficient and reliable mechanism for connecting the proximal ends of bipolar temporary pacing wires to a pacing or monitoring instrument. The mechanism should have few parts, be easy to manufacture and be consistent with minimal tissue trauma to the patient.

BRIEF SUMMARY OF THE INVENTION

An object of this invention is to provide a novel and improved surgical electrical connector that can be connected to a medical instrument in a simple and timesaving manner.

Another objective of the invention is to provide an electrical connector that can be electrically connected directly to the socket of a pacing or monitoring instrument. A further object of the invention is to provide an assembly requiring minimal tissue trauma during installation and simultaneously allowing for two electrical connections to be established with a pacing or monitoring instrument.

An additional object of the invention is to provide an electrical connector with partially insulated ends.

Still another object of the invention is to provide an electrical connector assembly that is smaller in diameter than the Keith-type needle used to guide the connector to the outside of the body.

With the foregoing objects in mind, the present invention relates to an electrical connector assembly in which a conductive lead adapted for connection to a source of electrical signals is folded over on itself. The present invention is especially suited for use in conjunction with a temporary cardiac pacing wire which includes an electrically conductive flexible wire having two elongated conductive sections at its proximal end. The conductive sections can be plugged a pair of socket-like terminals of a pacing or monitoring instrument which generates electrical signals for stimulating, pacing, sensing, monitoring or defibrillating the heart of a patient. One conductive section results from the distal end of a Keith-type needle that breaks away from the needle. This section can be plugged directly into one of the socket-like terminals of the pacing or monitoring instrument. The other conductive section is suitable for connecting to the other socket-like terminal when folded over on itself, or an adjacent insulated portion of wire, to provide dimensional thickness necessary for an electrically secure connection. To facilitate its connection to the pacing or monitoring instrument in a plug-like fashion, this section may have a length which is more than ten times the diameter of the Keith-type needle, while having a maximum lateral dimension (e.g., a diameter in the case of a circular cross section) which is smaller than or equal to the diameter of the Keith-type needle.

The invention has the advantage of ease of use without requiring additional pin-plugs or other assemblies. Also, the invention allows the use of needles, wires and connectors sized smaller than or equal to the size of existing Keith-type needles.

BRIEF DESCRIPTION OF THE DRAWINGS

For a better understanding of the present invention, reference is made to the following detailed description of various exemplary embodiments considered in conjunction with the accompanying drawings, in which:

FIG. 1 is a schematic illustration of a first embodiment of the invention showing a bipolar temporary pacing wire including a distal anchoring portion;

FIG. 1A is a cross-sectional view of the first embodiment taken along section line I—I and looking in the direction of the arrows;

FIG. 1B is a cross-sectional view of the first embodiment taken along section line II—II and looking in the direction of the arrows;

FIG. 7 is a schematic, partially cross-sectioned illustration of a fifth embodiment of the invention inserted into a pacemaker; and FIG. 7A is a cross-sectional view of the fifth embodiment taken along section line III—III and looking in the direction of the arrows.

DETAILED DESCRIPTION OF THE INVENTION

Figure 2:
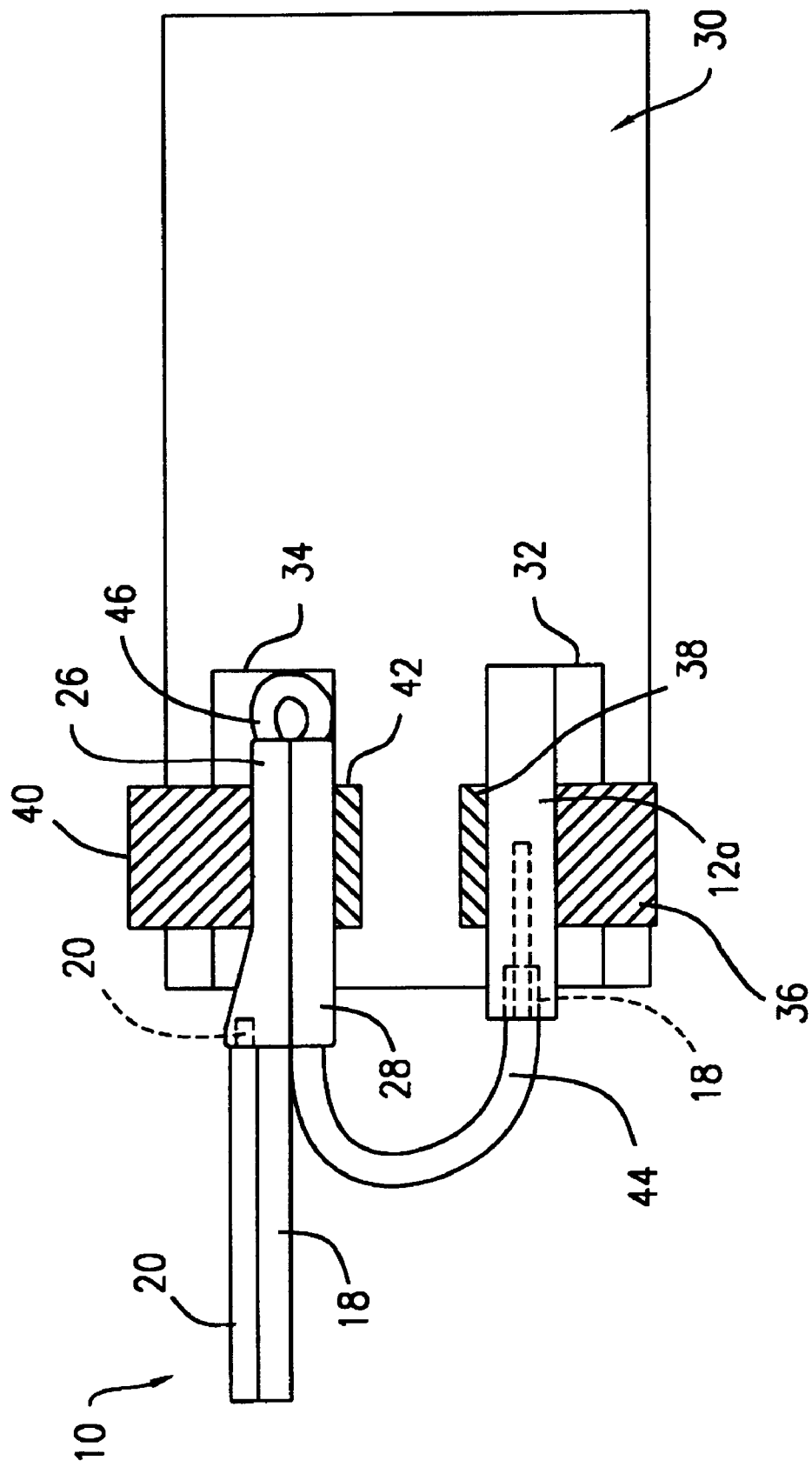
FIG. 2 is a schematic, partially cross-sectioned illustration of the first embodiment inserted into a pacemaker.

Although the present invention is applicable to many different types of cardiac devices, it is especially suitable for use in conjunction with a bipolar temporary cardiac pacing wire. Accordingly, the present invention will be described below in connection with such a pacing wire.

As used herein, the term "distal" shall mean that portion of the pacing wire or element thereof which is remote from a source of electric signals located external to the patient's body. Conversely, the term "proximal" shall mean that portion of the pacing wire or element thereof which is in close proximity to the external source of electrical signals.

Referring to FIG. 1, a bipolar temporary cardiac pacing wire 10 includes a Keith-type breakaway needle 12 arranged at a proximal end of the pacing wire 10 and a curved needle 14 arranged at a distal end of the pacing wire 10, which also includes any type of suitable anchor 16 such as the one disclosed in U.S. patent application Ser. No. 09/307,537, which was filed on May 7, 1999 by the assignee of the present application and which is incorporated herein by reference. The Keith-type needle 12, such as the one disclosed in U.S. Pat. No. 4,010,756 issued on Mar. 8, 1977 to DuMont et al., has a distal section 12a and a proximal section 12b, which is pointed for piercing the thoracic wall to lead the proximal end of the pacing wire 10 outside the chest cavity of a patient in accordance with a medical procedure well known in this field. The curved needle 14 is adapted to pierce the heart tissue and to attach the anchor 16 to the heart in accordance with another well-known medical procedure.

A pair of insulated, electrically conductive electrode wires 18, 20 extends between the distal and proximal ends of the pacing wire 10. The electrode wires 18, 20 are of the "lamp cord" type (i.e., they are arranged in a side-by-side fashion as shown in FIG. 1A), each wire having a braided, multistrand core of stainless steel and a surrounding layer of insulation made from polyethylene. Alternatively, the core of each wire could have a twisted construction with a surrounding layer of insulation made from polyethylene or any other suitable electric non-conducting material, such as silicon, polytetrafluoroethylene, or nylon.

At the distal end of the pacing wire 10 there are two electrodes 22, 24. The electrode 22 is electrically and mechanically connected to the electrode wire 18, but only mechanically connected to the electrode wire 20, which passes through the sleeve-like electrode 22 and is mechanically and electrically connected to the electrode 24. The electrodes 22, 24 have a conventional construction and are adapted to transmit electrical signals from one to the other for the purpose of stimulating, pacing, sensing, monitoring, or defibrillating the heart.

At the proximal end of the pacing wire 10 there are two connectors 26, 28. The connector 26 is mechanically and electrically connected to the electrode wire 20, but only mechanically connected to the electrode wire 18, which passes through the elongated, sleeve-like connector 26 and which is mechanically and electrically connected to the Keith-type needle 12 in a conventionally manner. The other elongated, sleeve-like connector 28 is positioned on the electrode wire 18 intermediate to the connector 26 and the Keith-type needle 12. Unlike the connector 26, which is electrically connected to the electrode wire 20, the connector 28 does not have to be electrically connected to either of the electrode wires 18, 20. However, the connector 28 may be electrically connected to the electrode wire 20, which could also be electrically connected to both of the connectors 26, 28. Each of the connectors 26, 28 extends circumferentially about the electrode wire 18 (see, for example, FIG. 1B) and is made from suitable electrically conductive material, such as stainless steel, for a purpose to be described hereinafter. While the connectors 26, 28 have a generally circular cross-sectional shape (as shown, for example, in FIG. 1B), they could have other cross-sectional shapes, such as oval, square, rectangular, etc.

Referring now to FIG. 2, the pacing wire 10 is shown adapted for use in connection with a pacemaker 30 having a pair of sockets 32, 34. As is typical of pacemakers like the pacemaker 30, a pair of spring-loaded clamps 36, 38 is mounted in the socket 32, one of which carries an electrical charge (either positive or negative) and the other of which is neutral (it does not carry either a positive charge or a negative charge). In a similar and typical fashion, a pair of spring-loaded clamps 40, 42 is mounted in the socket 34, one of which is neutral and the other of which carries an electrical charge opposite the charged clamp in the socket 32 (e.g., if the charged clamp in the socket 32 carries a negative charge, then the charged clamp in the socket 34 carries a positive charge, and vice versa).

In order to make an electrical connection within the socket 32 of the pacemaker 30, the Keith-type needle 12 is severed intermediate to its ends and the distal section 12a is inserted into the socket 32, while the proximal end 12b is discarded. Inside the socket 32, the distal section 12a is gripped between the clamps 36, 38 which have concave-shaped gripping surfaces so as to make good electrical and/or mechanical contact with the cylindrically-shaped distal section 12a and hence the electrode wire 18. Because the distal section 12a is made entirely of an electric-conducting material, such as stainless steel, electric-conducting contact within the socket 32 is ensured, regardless of which of the clamps 36, 38 is charged and regardless of how the distal section 12a is oriented relative to the charged clamp.

In order to make an electrical connection within the socket 34 of the pacemaker 30, the electrode wire 18 is first folded over onto itself such that the connectors 26, 28 are arranged in an abutting, juxtaposed relationship with respect to each other (i.e., they extend conjointly in parallel directions along their lengths). The folded portion containing the side-by-side connectors 26, 28 is then inserted, in a plug-like fashion, into the socket 34, where it is gripped between the clamps 40, 42 with the connector 26 in electric-conducting contact with the clamp 40 and the connector 28 in mechanical, but not electrical, contact with the clamp 42. To ensure good electrical and/or mechanical contact with the cylindrically-shaped connectors 26, 28, the clamps 40, 42 have concave gripping surfaces. Because the connectors 26, 28 are in electric-conducting contact with each other, it does not matter which of the clamps 40, 42 is charged. More particularly, if, on the other hand, the clamp 40 is charged, then electric signals will flow from the pacemaker 30 to the electrode wire 20 via the clamp 40 and the connector 26. If, on the other hand, the clamp 42 is charged, then electric signals will flow from the pacemaker 30 to the electrode wire 20 via the clamp 42, the connector 28 and the connector 26.

Still referring to FIG. 2, the electrode wire 18 is flexible enough to form a loop 44 in the segment between the connector 28 and the distal section 12a of the Keith-type needle. In addition, the electrode wire 18 has sufficient flexibility to form a loop 46 in the segment between the connectors 26, 28. The loop 46 is small enough so as not to inhibit the folded section of the electrode wire (i.e., the plug-like section with the side-by-side connectors 26, 28) from being inserted into the socket 34. When arranged in the side-by-side manner depicted in FIG. 2, the cumulative size of the connectors 26, 28 is sufficiently large to avoid a poor (i.e., loose) grip by the clamps 40, 42, thereby promoting a good electrical connection between the pacemaker 30 and the electrode wire 20.

While the actual length of each of the connectors 26, 28 needs only be sufficient to assure secure inserted into the socket 34 of the pacemaker 30, preferably this length is about ten times or greater than ten times the diameter of the Keith-type needle 12. It is also preferable that each of the connectors 26, 28 has a diameter which is smaller than or equal to that of the Keith-type needle 12. If the connectors 26, 28 do not have a circular cross-sectional shape, then their maximum lateral dimension would be smaller than or equal to the diameter of the Keith-type needle 12.

To fabricate the connector 26, a 300 series stainless steel tube (Type 304 Stainless Steel Hypodermic Needle Tubing Catalog No. T19XXTW available from Popper & Sons, Inc., New Hyde Park, N.Y.) of 0.019", 0.037" inside diameter was used. The proximal end of the tube was reduced in diameter using a rotating Torrington swaging press (MIN 9194, made by Torrington Swager-Vaill End Forming Machinery Inc., Waterbury, Conn.), while the distal end was left as its original diameter. The ends of the electrode wires 18, 20 were separated for a length sufficient to allow for the electrode wire 18 to extend on for attachment to the distal section 12a of the Keith-type needle 12. The electrode wire 20 was cut and the insulation removed from a small length of its end. Both of the electrode wires 18, 20 were then inserted into the distal opening (i.e., the larger one) of the swaged tube until the uninsulated end of the electrode wire 20 was completely inside the distal opening of the tube. The end of the tube containing the distal opening was then swaged to make a secure electrical connection between the uninsulated end of the electrode wire 20 and the tube. While the swaging operation was carried out using a Torrington swaging press, a multi-collet vice could also be used to achieve a similar result.

The connector 28 was fabricated in a similar manner. More particularly, the electrode wire 18 was placed in a 0.019" inside diameter 300 stainless steel tubing (Popper & Sons, Inc.). The electrode wire 18 and the tubing wire then placed in a Torrington swaging press and swaged until the diameter of the tubing was reduced sufficiently to assure a secure circumferential fit around the electrode wire 18 without compromising the wire's insulation.

What follows is a description of various alternate embodiments of the present invention. In describing these embodiment, elements corresponding to elements described above in connection with the embodiment of FIGS. 1 and 2 will be described by corresponding reference numerals increased by one hundred, two hundred, three hundred and four hundred, respectively. The alternate embodiments are constructed and operate in the same manner as the embodiment of FIGS. 1 and 2, unless otherwise specified.

Figure 3:
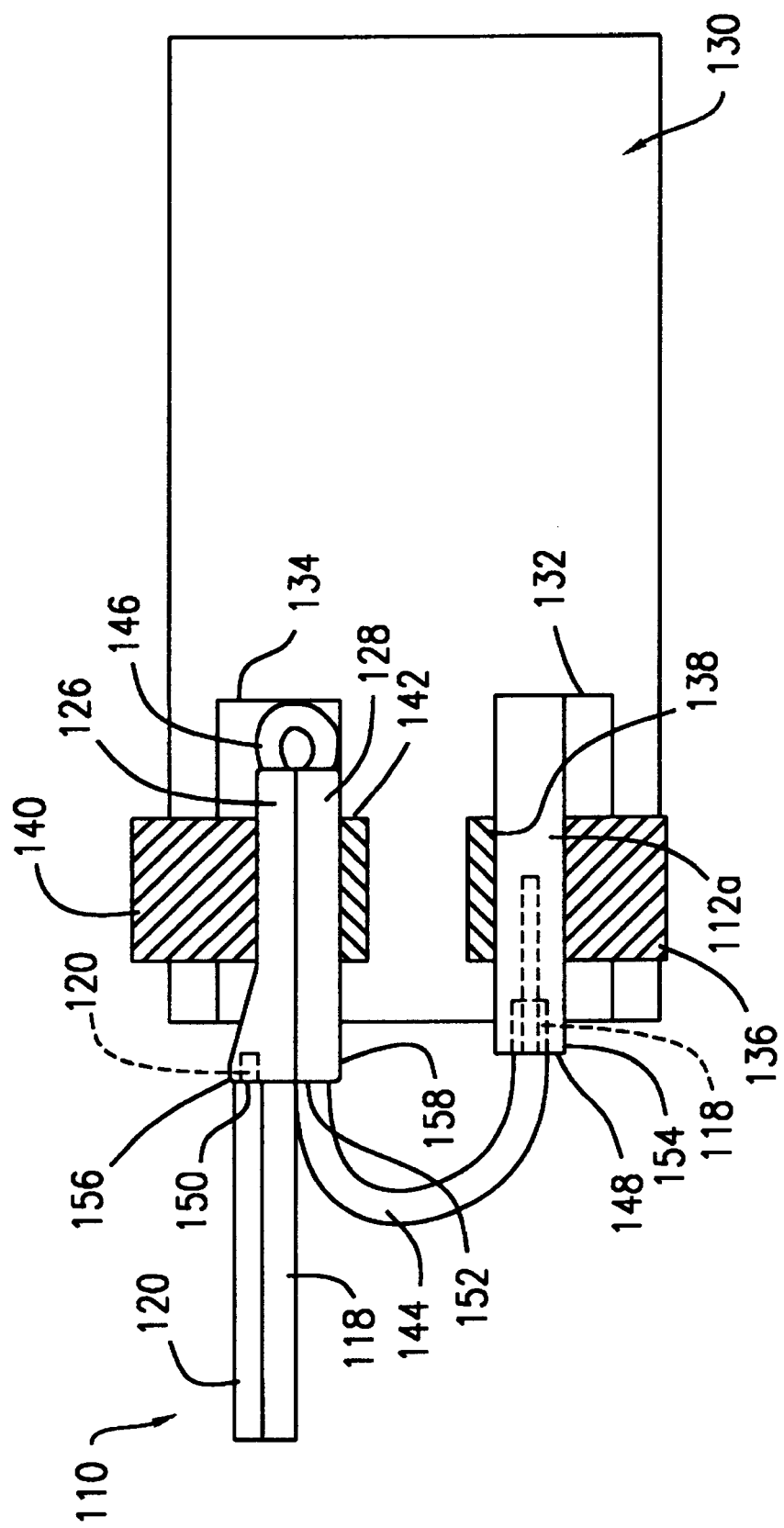
FIG. 3 is a schematic, partially cross-sectioned illustration of a second embodiment of the invention inserted into a pacemaker.

With reference to FIG. 3, the distal section 112a of a severed Keith-type needle has an end 148 which is exposed in that it extends outwardly from the socket 132 of the pacemaker 130. Similarly, the connectors 126,128 has ends 150,152, respectively, which are exposed in that they extend outwardly from the socket 134 of the pacemaker 130. In order to prevent shorting or shocking problems, the exposed end 148 of the distal section 112a is provided with electric insulation 154, while the exposed ends 150,152 of the connectors 126, 128 are also provided with electric insulation 156, 158, respectively.

Figure 4:
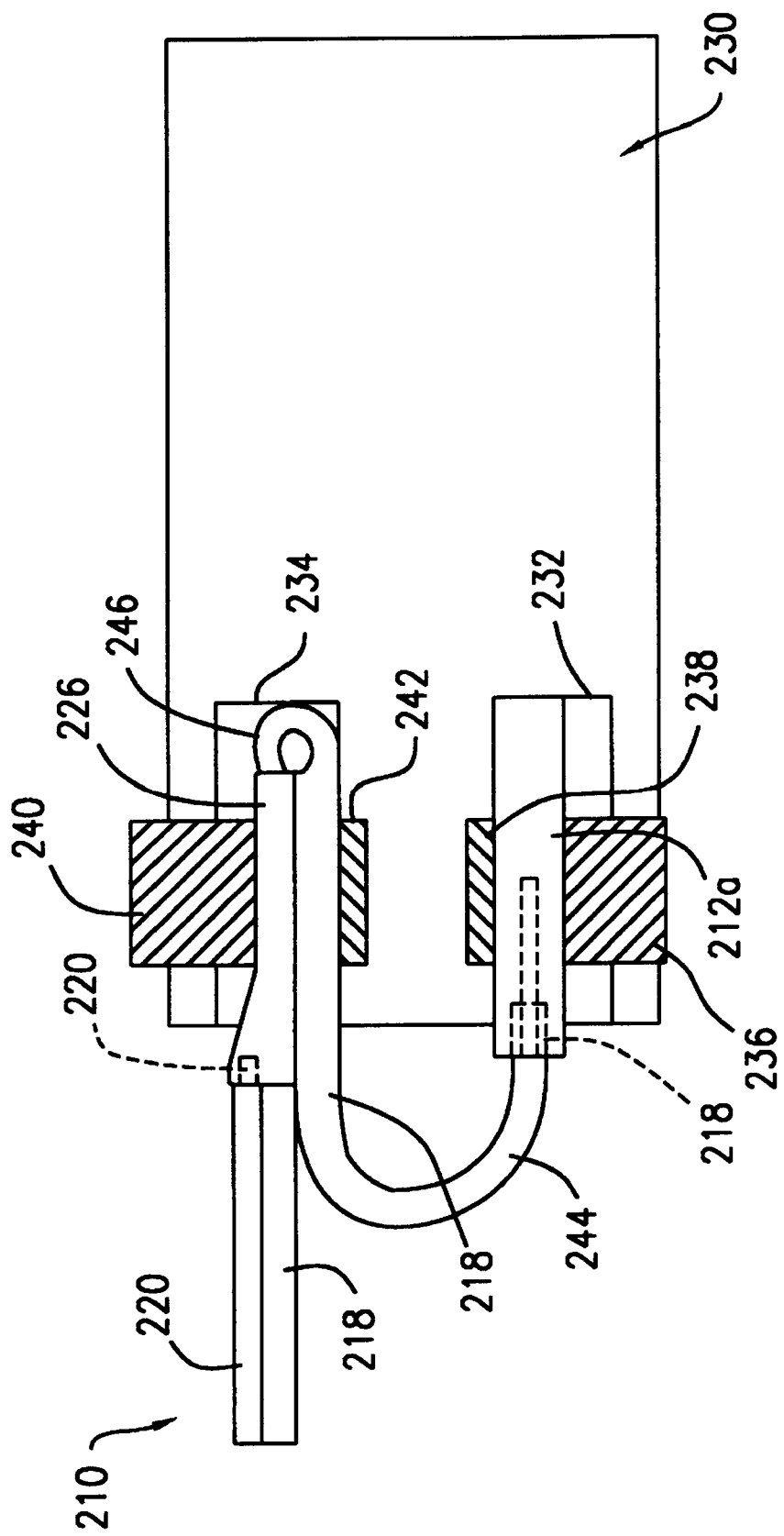
FIG. 4 is a schematic, partially cross-sectioned illustration of a third embodiment of the invention inserted into a pacemaker.

Referring now to FIG. 4, the socket 234 of the pacemaker 230 (such as a Medtronic Model No. 5375) houses the clamps 240, 242, both of which carry an electric charge. In this embodiment, unlike the embodiment of FIGS. 1 and 2, the connector 226 can receive electric signals from either of the clamps 240, 242, thereby making the connector 28 shown in FIGS. 1 and 2 expendable. Thus, although the electrode wire 218 still has a folded, plug-like portion, the connector 226 simply extends alongside the insulation on an abutting section of the electrode wire 218. As depicted in FIG. 4, electric signals would be transmitted from the pacemaker 230 to the electrode wire 220 via the clamp 240 and the connector 226. However, electric signals from the pacemaker 230 could also be transmitted to the electrode wire 220 if the connector 226 were in contact with the clamp 242, rather than the clamp 240.

Figure 5:
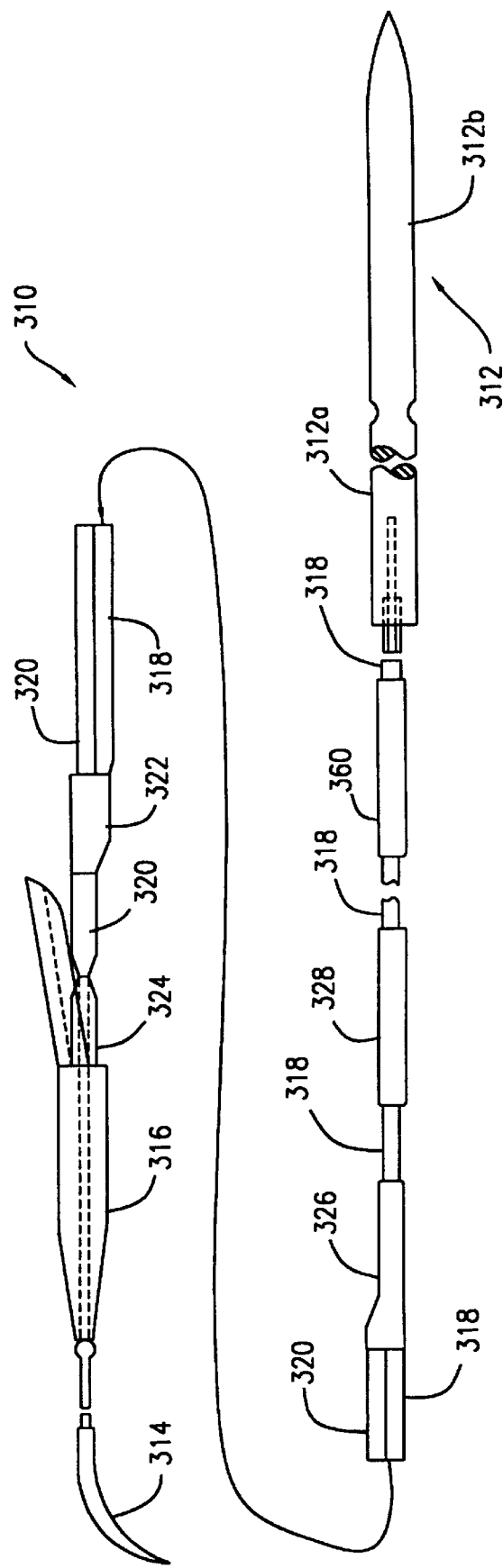
FIG. 5 is a schematic illustration of a fourth embodiment of the invention showing a bipolar temporary pacing wire including a distal anchoring portion.
Figure 6:
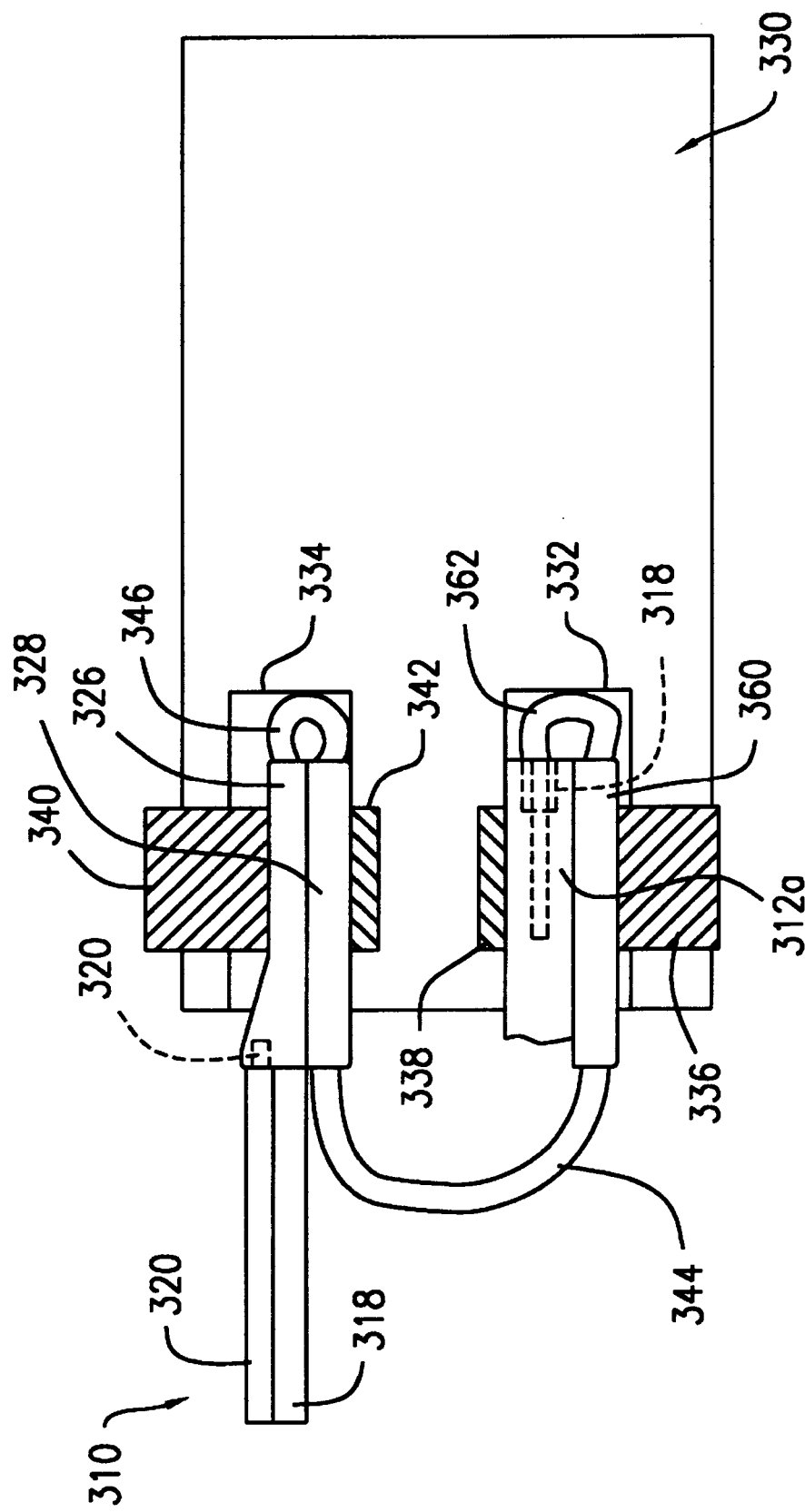
FIG. 6 is a schematic, partially cross-sectioned illustration of the fourth embodiment inserted into a pacemaker.

The embodiment of FIGS. 5 and 6 is especially useful with Keith-type needles having a diameter that is too small to be securely gripped by the clamps of a pacemaker like the Medtronic Model No. 5375. In this embodiment, the electrode wire 318 has a third sleeve-like connector 360, in addition to the connectors 326, 328. In order to make an electrical connection in the socket 332 of the pacemaker 330, the distal section 312a of a severed Keith-type needle is folded over onto the connector 360 in much the same way that the connectors 326, 328 are folded over onto each other, thereby forming a loop 362 in the segment of the electrode wire 318 between the distal section 312a and the connector 360. Like the side-by-side connectors 326, 328 which are inserted together into the socket 334, the distal section 312a and the connector 360 are inserted together, in plug-like fashion, into the socket 332, the loop 362 being small enough so as not to inhibit such insertion. Once they have been fully inserted into the socket 332, the distal section 312a makes electrical contact with the clamp 338, while the connector 360 makes electrical contact with the clamp 336. Of course, this arrangement could be reversed, whereby the distal section 312a would make electrical contact with the clamp 336, while the connector 360 would make electrical contact with the clamp 338. It should be noted that the connector 360 may or may not be electrically connected to the electrode wire 318 to which it is mechanically attached about the circumference thereof.

In the embodiment of FIGS. 7 and 7A, the electrode wires 418, 420 have a coaxial construction (see FIG. 7A). Except for the sizes and shapes of the connectors 426, 428, the other components of the pacing wire 410 are essentially the same as their counterparts in the embodiment of FIG. 2.

It will be understood that the embodiments described herein are merely exemplary and that a person skilled in the art may make many variations and modifications without departing from the spirit and scope of the invention. All such variations and modifications are intended to be included within the scope of the invention as defined in the appended claims.

What is claimed is:

1. An electrical connector for a cardiac device, comprising wire means having a distal end and a proximal end; and connecting means for electrically connecting said wire means to a cardiac device, said connecting means including at least one electrically conductive connector disposed about said wire means intermediate said distal and proximal ends thereof and a folded over section of said wire means which cooperates with said at least one connector to form a plug assembly having a dimensional thickness sufficient to permit said assembly to be plugged into an electrical terminal socket of the cardiac device.

2. An electrical connector according to claim 1, wherein said at least one connector includes a first connector and a second connector, one of said first and second connectors being located on said folded over section of said wire means, and said first and second connectors cooperating with each other and with said wire means to form said plug assembly.

3. An electrical connector according to claim 2, wherein said at least one electrical connector includes a third connector, and wherein said wire means includes a fourth electrically conductive connector disposed at said proximal end thereof, said fourth connector cooperating with said third connector and with another folded over section of said wire means to form another plug assembly having a dimensional thickness sufficient to permit said another assembly to be plugged into another electrical terminal socket of the cardiac device.

4. An electrical connector according to claim 1, wherein said at least one electrical connector includes one connector only, said one connector cooperating with an electrically insulated portion of said folded over section of said wire means to form said plug assembly.

5. An electrical connector for a cardiac device, comprising wire means having a first electrode at a distal end of said wire means a second electrode at said distal end of said wire means, a first electrically conductive wire electrically connected to said first electrode and extending from said first electrode to a proximal end of said wire means, and a second electrically conductive wire electrically connected to said second electrode and extending from said second electrode to said proximal end of said wire means; and connecting means for electrically connecting said wire means to a cardiac device, said connecting means including a folded over section of said wire means, a first connector, located at said proximal end of said wire means, for electrically connecting said first wire to a source of electric signals, and a second connector, located between said proximal and distal ends of said wire means, for electrically connecting said second wire to a source of electric signals, said second connector being in the form of a sleeve and being mechanically connected to said first and second wires but electrically connected to said second wire only, and said first wire including said folded over section.

6. An electrical connector according to claim 5, wherein said first wire is sufficiently flexible to permit a portion thereof to be folded over into abutment with said second connector to form a plug assembly having a dimensional thickness sufficient to permit said assembly to be plugged into an electrical terminal socket.

7. An electrical connector according to claim 6, wherein said first connector includes a distal portion of a severed Keith-type needle.

8. An electrical connector according to claim 7, wherein said Keith-type needle has an outside diameter and said second connector has a length which is at least about ten times said diameter of said Keith-type needle.

9. An electrical connector according to claim 8, wherein said second connector has a maximum lateral dimension which is not greater than said diameter of said Keith-type needle.

10. An electrical connector according to claim 7, wherein said connecting means further includes a third connector which is in the form of a sleeve and which is mechanically connected to said first wire, said third connector being positioned on said first wire such that said third connector cooperates with said second connector to form said plug assembly.

11. An electrical connector according to claim 10, wherein said third connector is electrically connected to said second wire.

12. An electrical connector according to claim 10, wherein said third connector is not electrically connected to said second wire.

13. An electrical connector according to claim 10, wherein said second and third connectors extend circumferentially about said first wire, said first wire extending longitudinally through said second and third connectors.

14. An electrical connector according to claim 10, wherein said Keith-type needle has an outer diameter and each of said second and third connectors has a length which is at least about ten times said diameter of said Keith-type needle and a maximum lateral dimension which is not greater than said diameter of said Keith-type needle.

15. An electrical connector according to claim 10, wherein said second connector has an electrically-insulated distal end, said third connector has an electrically-insulated proximal end, and said distal portion of said Keith-type needle has an electrically-insulated distal end.

16. An electrical connector according to claim 10, wherein said connecting means further includes a fourth connector which is in the form of a sleeve and which extends circumferentially about said first wire, said fourth connector being positioned on said first wire such that said fourth connector abuts said distal portion of said Keith-type needle when another section of said wire means is folded over, whereby said fourth connector cooperates with said distal portion of said Keith-type needle to form another plug assembly adapted to be plugged into another electrical terminal socket.

17. An electrical connector according to claim 16, wherein said fourth connector is electrically connected to said first wire.

18. An electrical connector according to claim 16, wherein said fourth connector is not electrically connected to said first wire.

19. An electrical connector according to claim 16, wherein said Keith-type needle has an outer diameter and each of said second, third, and fourth connectors has a length which is at least ten times said diameter of said Keith-type needle and a maximum lateral dimension which is not greater than said diameter of said Keith-type needle.

20. An electrical connector according to claim 5, wherein said first and second wires are arranged in a side-by-side fashion relative to each other.

21. An electrical connector according to claim 5, wherein said first and second wires are arranged coaxially relative to each other.

22. A temporary pacing wire, comprising a first electrode at a distal end of said pacing wire; a second electrode at said distal end of said pacing wire; a first electrically conductive wire electrically connected to said first electrode and extending from said first electrode to a proximal end of said pacing wire; a second electrically conductive wire electrically connected to said second electrode and extending from said second electrode to said proximal end of said pacing wire; first connecting means, located at said proximal end of said pacing wire, for electrically connecting said first wire to a source of electric signals; and second connecting means, located at said proximal end of said pacing wire, for electrically connecting said second wire to a source of electric signals, said second connecting means including a connector which is in the form of a sleeve and which is mechanically connected to said first and second wires but electrically connected to said second wire only, said first wire being sufficiently flexible to permit a portion thereof to be folded over into abutment with said connector to form a plug assembly having a dimensional thickness sufficient to permit said assembly to be plugged into an electrical terminal socket.

* * * * *